(12) United States Patent
Nickel et al.

(10) Patent No.: US 7,452,910 B2
(45) Date of Patent: *Nov. 18, 2008

(54) INDOLYL-3-GLYOXYLIC ACID DERIVATIVES HAVING THERAPEUTICALLY VALUABLE PROPERTIES

(75) Inventors: Bernd Nickel, Mühltal (DE); Gerald Bacher, Heidelberg (DE); Thomas Klenner, Ingelheim (DE); Thomas Beckers, Frankfurt (DE); Peter Emig, Bruchköbel (DE); Jürgen Engel, Alzenau (DE); Erik Bruyneel, Harelbeke (BE); Günter Kamp, Münster (DE); Kirsten Peters, Münster (DE)

(73) Assignee: ZIOPHARM Oncology, Inc., Boston, MA (US)

( * ) Notice: Subject to any disclaimer, the term of this patent is extended or adjusted under 35 U.S.C. 154(b) by 7 days.

This patent is subject to a terminal disclaimer.

(21) Appl. No.: 10/686,809

(22) Filed: Oct. 17, 2003

(65) Prior Publication Data
US 2004/0171668 A1 Sep. 2, 2004

Related U.S. Application Data

(63) Continuation of application No. 09/492,531, filed on Jan. 27, 2000, now Pat. No. 6,693,119, which is a continuation-in-part of application No. 09/285,058, filed on Apr. 2, 1999, now Pat. No. 6,232,327.

(30) Foreign Application Priority Data

Apr. 2, 1998 (DE) .................. 198 14 838
Sep. 28, 1999 (DE) .................. 199 46 301

(51) Int. Cl.
*A61K 31/44* (2006.01)

(52) U.S. Cl. ....................................... 514/339
(58) Field of Classification Search ................. 514/339, 514/337
See application file for complete search history.

(56) References Cited

U.S. PATENT DOCUMENTS 5,405,864 A 4/1995 Broka (Continued)

FOREIGN PATENT DOCUMENTS

DE 2315989 10/1973

(Continued)

OTHER PUBLICATIONS

Gura et al. (Science, 1997, 278:1041-1042.*

(Continued)

*Primary Examiner*—Ardin Marschel
*Assistant Examiner*—James D Anderson
(74) *Attorney, Agent, or Firm*—Ropes & Gray LLP

(57) ABSTRACT

The invention relates to the use of N-substituted indole-3-glyoxylamides of the general Formula I:

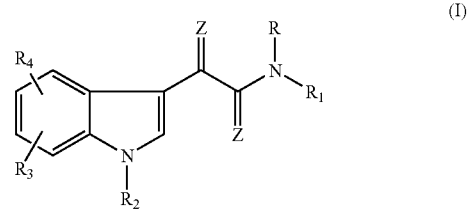

Figure 1:
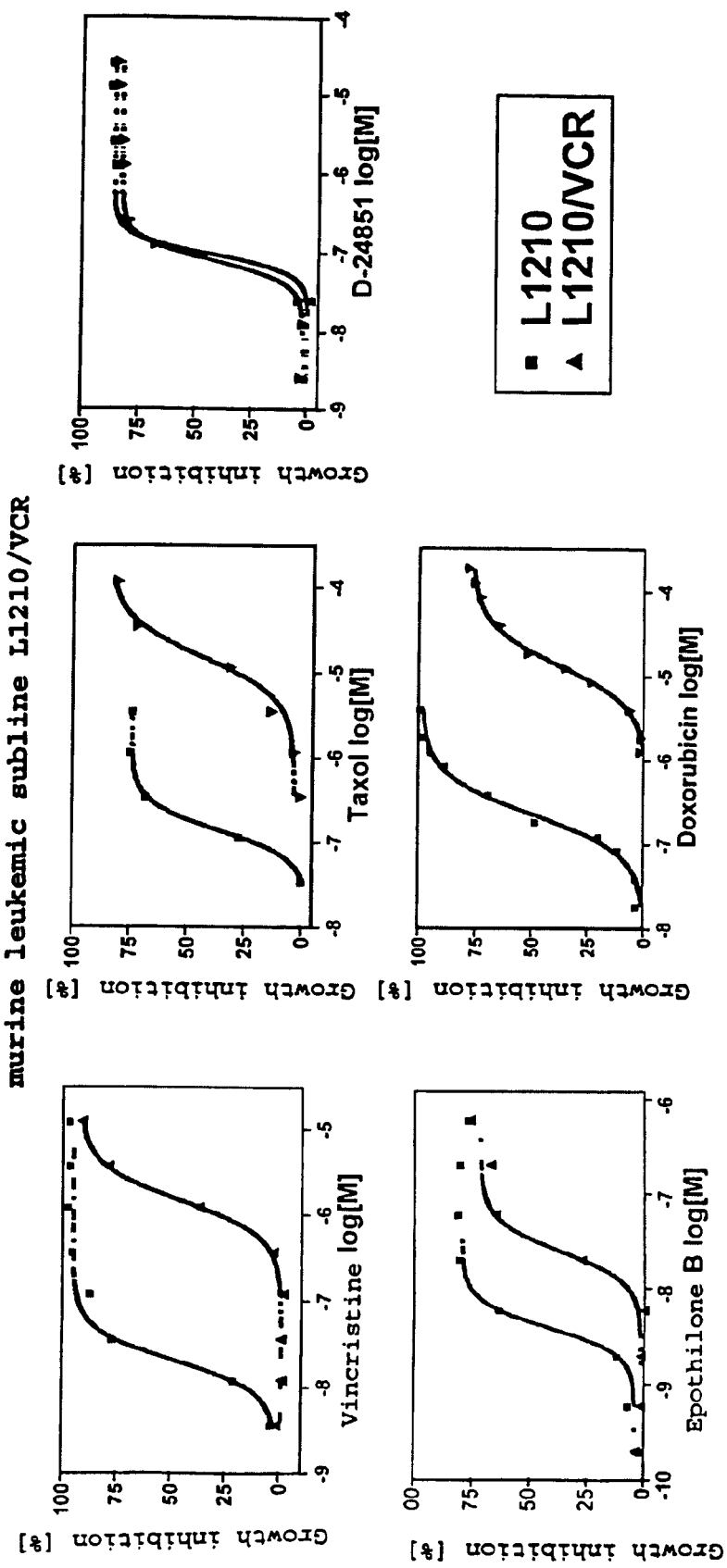

and to pharmaceutical compositions having antitumor action.

13 Claims, 9 Drawing Sheets

* In contrast to Taxol, doxorubicin, vincristine or epothilone B, D-24851 has the same cytotoxic activity against the MDR mouse leukemic subline L1210/VCR as against the normal LL1210

U.S. PATENT DOCUMENTS

| | | | |
|---|---|---|---|
| 6,008,231 | A | 12/1999 | Lebaut et al. |
| 6,225,329 | B1 | 5/2001 | Richter et al. |
| 6,232,327 | B1 | 5/2001 | Nickel et al. |
| 6,251,923 | B1 | 6/2001 | Hofgen et al. |
| 6,262,044 | B1 | 7/2001 | Moller et al. |
| 6,344,467 | B1 | 2/2002 | Lebaut et al. |
| 6,432,987 | B2 | 8/2002 | Gunther et al. |
| 6,693,119 | B2 | 2/2004 | Nickel et al. |
| 2004/0266762 | A1 | 12/2004 | Gerlach |
| 2006/0040991 | A1 | 2/2006 | Roessler |
| 2006/0280787 | A1 | 12/2006 | Roessler et al |

FOREIGN PATENT DOCUMENTS

| | | |
|---|---|---|
| DE | 196 36 150 A1 | 2/1998 |
| JP | 2000-239252 | 9/2000 |
| WO | WO-98/09946 | 3/1998 |
| WO | WO 99/46237 | 9/1999 |
| WO | WO 99/51224 | 10/1999 |
| WO | WO 99/55696 | 11/1999 |
| WO | WO 00/67802 | 11/2000 |

OTHER PUBLICATIONS

Johnson et al. (British J. of Cancer, 2001, 84(10):1424-1431.*

Dupont et al. J. Cutan. Med. Surg., 1998, vol. 2, pp. 146-152 (Abstract attached).*

Caplus AN 1999:708761, Hofgen Norbert et al., RN 247584-34-5. (Abstract only).

Fiszer-Maliszewska et al., "Immunomodulation and Therapeutic Effects of Cytostatics," Zbl. Bakt. Suppl. 13, pp. 215-230 (1985).

Lipp et al., "Some derivatives of 5-benzyloxy-3-indolylglyoxylic acid," CA 52:18374 (1958).

Ooi Ve, Liu F., Curr. Med. Chem. Jul. 7, 2000(7):715-29, NCBI abstract.

Podwinski et al., "Synthesis of some 5-benzyloxyindole-3-glyoxylic acid amides," CA 70(9):37598 (1969).

Bacher, et al., "D-24851, a Novel Synthetic Microtubule Inhibitor, Exerts Curative Antitumoral Activity in Vivo, Shows Efficacy toward Multidrug-resistant Tumor Cells, and Lacks Neurotoxicity," Cancer Research, 61(1):392-399 (2001).

Evans et al., "Probing the 5-Ht$_3$ Receptor Site Using Novel Indole-3-Glyoxylic Acid Derivatives," Med. Chem. Res., 3:386-406 (1993).

Guenther et al., "Discovery and synthesis of novel N-substituted indoly-3-glyoxylic acid derivatives with tublin-binding activity as anti-cancer agents," Proceedings of the American Association for Cancer Research Annual Meeting, 41:769 (2000).

Raab et al., "ZIO-301 (Indibulin) a novel tubulin polymerization inhibitor has potent anti-tumor activity and a distinct tubulin site," Proceedings of the American Association for Cancer Research Annual Meeting, 48:337 (2007).

* cited by examiner

Influence of D-24851 on the multidrug-resistant murine leukemia L1210 (dose 10% of the $LD_{50}$)

| | Dose (mg/kg) | L1210 ILS % | L1210/VCR ILS % |
|---|---|---|---|
| D-24851 | 4 x 100 p.o. | 46 | 42 |
| | 4 x 147 p.o. | 94 | 85 |
| Adriamycin | 4 x 1 i.p. | 158 | 6 |
| Taxol | 4 x 15 i.p. | 82 | 6 |
| Vincristine | 4 x 0.2 i.p. | 47 | -11 |

*FIG. 3*

- D-24851 inhibits the migration of MO4 cells in a dose-dependent manner
  From this, an antiinvasive and an antimetastatic action can be derived for D-24851.

Neurotoxicity

| | D-24851<br>10x 20 mg/kg p.o | Vincristine<br>10x 0.2 mg/kg i.p. | Taxol<br>10x 15 mg/kg i.p. |
|---|---|---|---|
| Ataxia (rat) | -- | + | ++ |
| Traction (rat) | -- | + | ++ |
| Reaction (rat) | -- | ++ | +++ |

+ p ≥ 0.05 vs. control    ++ p ≥ 0.01 vs. control    -- = no effect

D-24851 shows no neurotoxicity [sic] in maximally antitumor-active doses in contrast to Taxol and vincristine

*FIG. 6*

FIG. 8
Angiogenesis in human endothelial cell culture
Vital staining, 44 hours after induction of angiogenesis
DMSO control
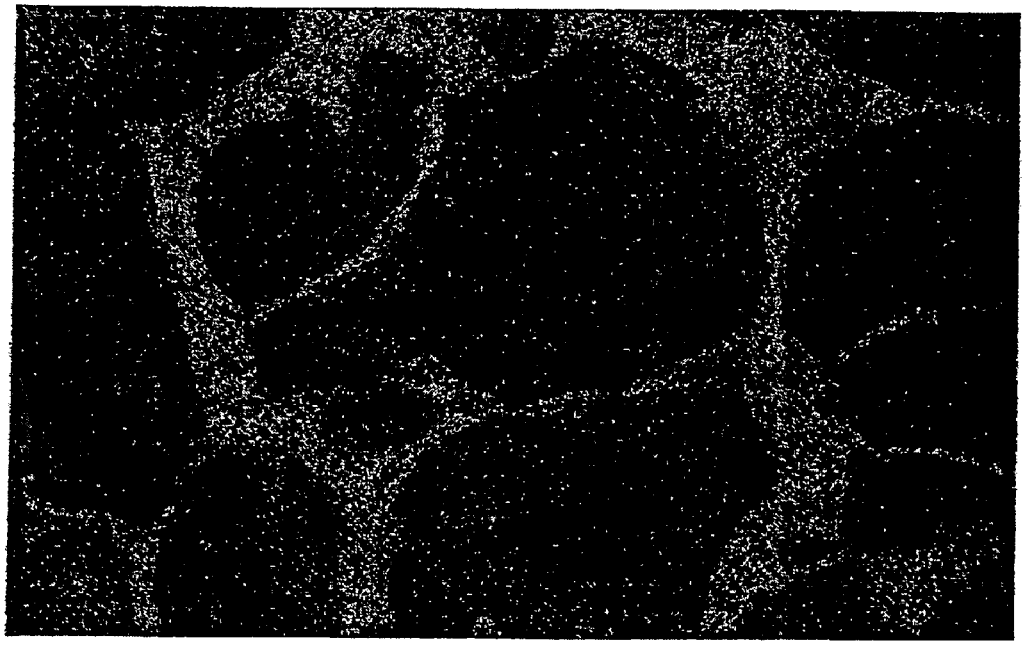
0.1 µM D24851
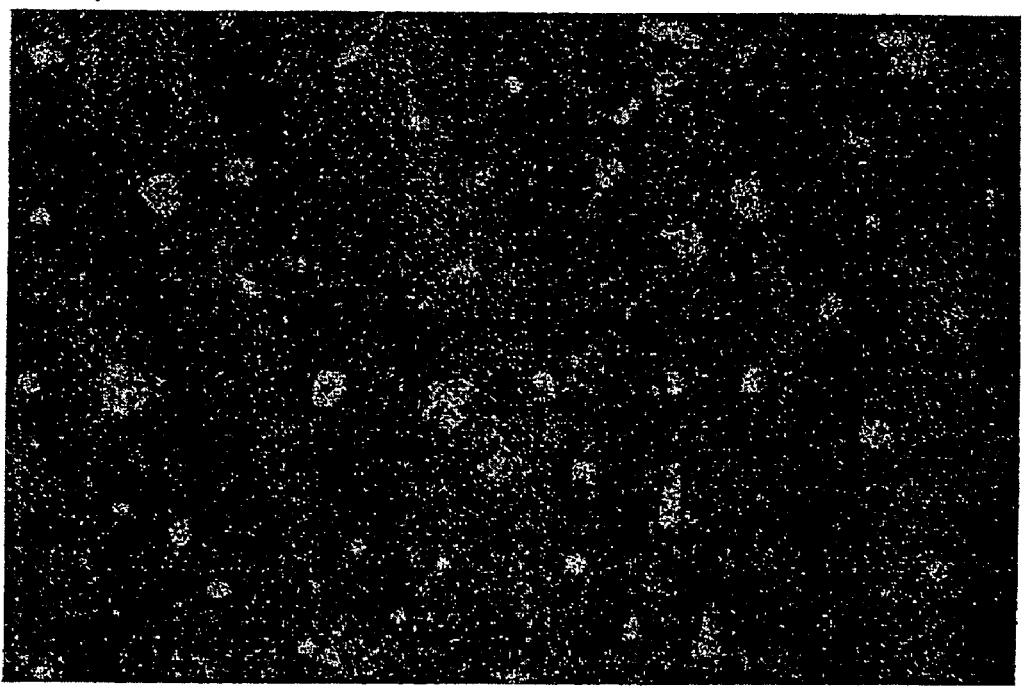

FIG. 9
Angiogenesis in human endothelial cell culture
Lethal staining, 22 hours after induction of angiogenesis
DMSO control
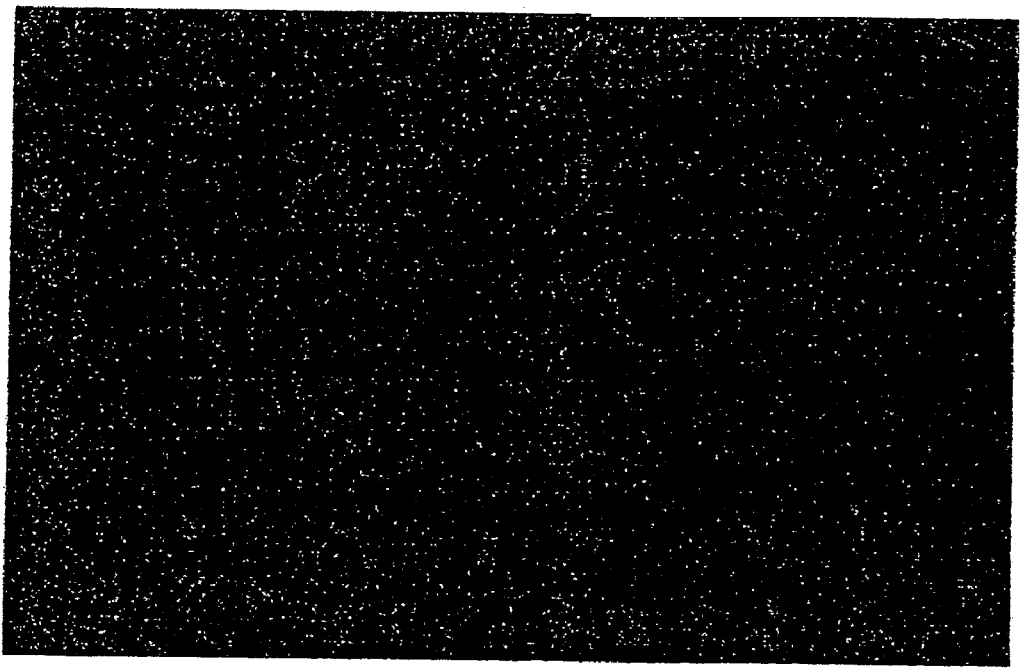
0.1 µM D24851
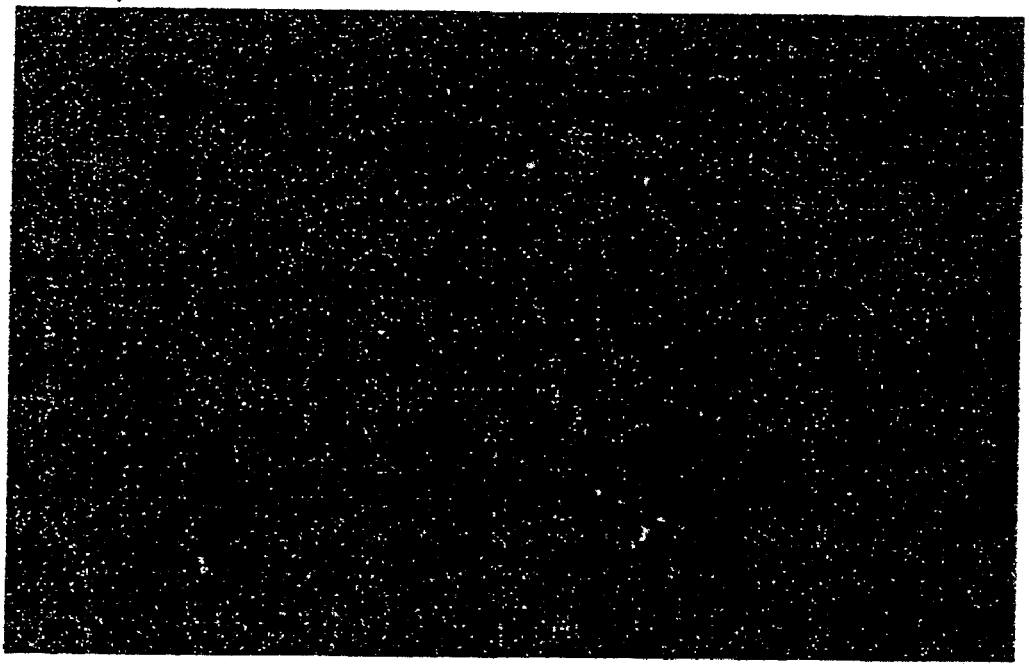

INDOLYL-3-GLYOXYLIC ACID DERIVATIVES HAVING THERAPEUTICALLY VALUABLE PROPERTIES

This is a continuation of U.S. patent application Ser. No. 09/492,531, filed Jan. 27, 2000 which is a continuation-in-part of U.S. patent Application Ser. No. 09/285,058, filed Apr. 2, 1999, which claims priority to German Appl. Nos. 19946301.8, filed Sep. 28, 1999 and 19814838.0, filed Apr. 2, 1998, all of which are incorporated herein in their entirety.

The invention relates to the further advantageous embodiment of the German Patent Application indole-3-glyoxylamides having the reference 19814 838.0.

In connection with chemotherapy in the case of oncoses, the greatest problems result due to the occurrence of pharmaceutical resistance on the one hand and due to the serious side effects of these agents on the other hand.

In addition, it is known that after reaching a certain size many primary tumors prematurely tend to metastasis formation via the blood stream and lymphatic tracts. The progressive process of tumor invasion and the formation of metastases is the most frequent cause of death of the cancer patients.

There are various approaches for explaining this spread, inter alia enhanced angiogenesis, increased extracellular matrix degradation, tumor cell migration and modulation of cell adhesion. These factors can also interact but to date are only partially resolved.

The metastatic spread of a tumor is usually accompanied by poor prognoses in tumor treatment. The prerequisite for metastatic spread is the detachment of cells from the primary tumor, the migration of cells to the blood vessels, invasion into the blood vessels and invasion of the cells from the blood vessels into other tissue.

An inhibitory action of certain oncostatic agents such as tamoxifen on the migration and invasion of cancer cells is known [J Clin Endocrinol Metab 1995 January; 80(1): 308-13].

The inhibition of tumor cell invasion by verapamil has been reported [Pigment Cell Res 1991 December; 4(5-6): 225-33].

The influence of melatonin on invasive and metastatic properties of MCF-7 human breast cancer cells has been reported [Cancer res 1998 Oct. 1; 58(19): 4383-90].

In the published PCT Application WO 96/23506, the overcoming of pharmaceutical resistance in certain tumor pharmaceuticals was demonstrated as a result of the gene amplification of the multi-drug resistance gene (MDR gene) brought about by such oncostatic agents.

Oncostatic agents such as vincristine and Taxol furthermore have a not inconsiderable neurotoxicity, which proves disadvantageous in chemotherapy.

The object of the invention is then to widen the field of use of N-substituted indole-3-glyoxylamides and thus to enrich the available pharmaceutical wealth. The possibility of a lower, longer-lasting and better-tolerable medication for the class of substances having antitumor action described in German Patent Application 19814 838.0 should thus be opened up. In particular, the disadvantageous development of resistance, as is known of many antitumor agents, should be circumvented.

Moreover, development and spread of the tumor due to metastases should be counteracted.

According to more recent knowledge, as angiogenesis is obviously responsible for tumor growth and the development of metastases, the property of angiogenesis inhibition represents a further advantageous pharmaceutical potential, for example, in cancer therapy.

The increase in action achieved with the N-substituted indole-3-glyoxylamides should more effectively shape pharmaceutical consumption in tumor therapy. Moreover, it should be possible to shorten the period of treatment and to extend it in therapy-resistant cases. In addition, relapses and metastases should be restricted or prevented and thus the survival period of the patients additionally increased. The aim is to develop medicaments which can intervene in the process of metastatic spread.

It has surprisingly been found that the N-substituted indole-3-glyoxylamides described in German Patent Application 19814 838.0, of the general formula 1 described below, which are suitable for the treatment of oncoses, further have those advantageous properties for tumor treatment which can extend their area of use.

The invention relates to the use of N-substituted indole-3-glyoxylamides according to claim 1 for tumor treatment in particular in the case of pharmaceutical resistance and metastasizing carcinoma and for the suppression of mestastasis formation, and also as angiogenesis inhibitors,

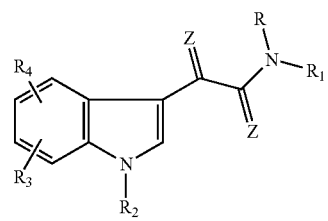

Formula 1 where the radicals R, $R_1$, $R_2$, $R_3$, $R_4$ and Z have the following meaning:

R=hydrogen, ($C_1$-$C_6$)-alkyl, where the alkyl group can be mono- or polysubstituted by the phenyl ring and this phenyl ring for its part can be mono- or polysubstituted by halogen, ($C_1$-$C_6$)-alkyl, ($C_3$-$C_7$)-cycloalkyl, by carboxyl groups, carboxyl groups esterified with $C_1$-$C_6$-alkanols, trifluoromethyl groups, hydroxyl groups, methoxy groups, ethoxy groups, benzyloxy groups and by a benzyl group which is mono- or polysubstituted in the phenyl moiety by ($C_1$-$C_6$)-alkyl groups, halogen atoms or trifluoromethyl groups, R is further selected from the benzyloxycarbonyl group (Z group) the tertiary-butoxycarbonyl radical (BOC radical), and the acetyl group;

$R_1$ can be a phenyl ring, which is mono- or polysubstituted by ($C_1$-$C_6$)-alkyl, ($C_1$-$C_6$)-alkoxy, cyano, halogen, trifluoromethyl, hydroxyl, benzyloxy, nitro, amino, ($C_1$-$C_6$)-alkylamino, ($C_1$-$C_6$)-alkoxycarbonylamino or by the carboxyl group or by the carboxyl group esterified with $C_1$-$C_6$-alkanols, or $R_1$ can be a pyridine structure of the formula 2

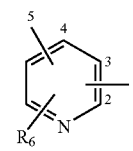

Formula 2 and its N-oxide, where the pyridine structure is alternatively bonded to the ring carbon atoms 2, 3 or 4 and can be substituted by the substituents $R_5$ and $R_6$. The radicals $R_5$ and $R_6$ can be identical or different and have the meaning $(C_1-C_6)$-alkyl $(C_3-C_7)$-cycloalkyl, $(C_1-C_6)$-alkoxy, nitro, amino, hydroxyl, halogen trifluoromethyl, ethoxycarbonylamino radical or the group carboxyalkyloxy in which the alkyl group can have 1-4 C atoms.

$R_1$ can further be a 2- or 4-pyrimidinyl heterocycle, where the 2-pyrimidinyl ring can be mono- or polysubstituted by methyl; a 2-, 3-, 4- or 8-quinolyl structure that may be substituted by $(C_1-C_6)$-alkyl, halogen, nitro, amino or $(C_1-C_6)$-alkylamino or; a 2-, 3-, or 4-quinolylmethyl group, where the ring carbons of the pyridylmethyl radical of the quinolyl group and of the quinolylmethyl radical may be substituted by $(C_1-C_6)$-alkyl, $(C_1-C_6)$-alkoxy, nitro, amino or $(C_1-C_6)$-alkoxycarbonylamino.

$R_1$, in the case in which R=hydrogen, the methyl or benzyl group and the benzyloxycarbonyl radical (Z radical), the tert-butoxycarbonyl radical (BOC radical) and the acetyl group, can furthermore be the following radicals: —$CH_2COOH$; —$CH(CH_3)$—$COOH$; $(CH_3)_2$—$CH$—$(CH_2)_2$—$CH$—$COO$—; $H_3C$—$H_2C$—$CH(CH_3)$—$CH(COOH)$—; $HO$—$H_2C$—$CH(COOH)$—; phenyl-$CH_2CH(COOH)$—; (4-imidazolyl)-$CH_2$—$CH$—$(COOH)$—; $HN$=$C(NH_2)$—$NH$—$(CH_2)_3$—$CH(COOH)$—; $H_2N$—$(CH_2)_4$—$CH(COOH)$—; $H_2N$—$CO$—$CH_2$—$CH$—$(COOH)$—; and $HOOC$—$(CH_2)_2$—$CH(COOH)$—

$R_1$, in the case in which R is hydrogen, the Z group, the BOC radical, the acetyl or the benzyl group, can furthermore be the acid radical of a natural or unnatural amino acid, e.g. the α-glycyl, the α-sarcosyl, the α-alanyl, the α-leucyl, the α-isoleucyl, the α-seryl, the α-phenylalanyl, the α-histidyl, the α-prolyl, the α-arginyl, the α-lysyl, the α-asparagyl and the α-glutamyl radical, where the amino groups of the respective amino acids can be present unprotected or can be protected. A possible protective group of the amino function is the carbobenzoxy radical (Z radical) and the tert-butoxycarbonyl radical (BOC radical) as well as the acetyl group. In the case of the asparagyl and glutamyl radical claimed for $R_1$, the second, unbonded carboxyl group is present as a free carboxyl group or in the form of an ester with $C_1-C_6$-alkanols, e.g. as a methyl, ethyl or as a tert-butyl ester. Furthermore, $R_1$, can be the allylaminocarbonyl-2-methylprop-1-yl group.

R and $R_1$, can further form, together with the nitrogen atom to which they are bonded, a piperazine ring of the formula III or a homopiperazine ring, provided $R_1$, is an aminoalkylene group, in which

Formula 3

$R_7$ is an alkyl radical, is a phenyl ring which can be mono- or polysubstituted by $(C_1-C_6)$-alkyl, $(C_1-C_6)$-alkoxy, halogen, a nitro group, an amino function or by the $(C_1-C_6)$-alkylamino group. ₇ is furthermore a benzhydryl group or a bis-p-fluorobenzhydryl group.

$R_2$ can be hydrogen and the $(C_1-C_6)$-alkyl group, where the alkyl group is mono- or polysubstituted by halogen and phenyl, which for its part can be mono- or polysubstituted by halogen, $(C_1-C_6)$-alkyl, $(C_3-C_7)$-cycloalkyl, carboxyl groups, carboxyl groups esterified with $C_1-C_6$-alkanols, trifluoromethyl groups, hydroxyl groups, methoxy groups, ethoxy groups or benzyloxy groups. The $(C_1-C_6)$-alkyl group counting as $R_2$ can further be substituted by the 2-quinolyl group and the 2-, 3- and 4-pyridyl structure, which can both in each case be mono- or polysubstituted by halogen, $(C_1-C_4)$-alkyl groups or $(C_1-C_4)$-alkoxy groups. $R_2$ is further the aroyl radical, where the aryl moiety on which this radical is based is the phenyl ring, which can be mono- or polysubstituted by halogen, $(C_1-C_6)$-alkyl, $(C_3-C_7)$-cycloalkyl, carboxyl groups, carboxyl groups esterified with $C_1-C_6$-alkanols, trifluoromethyl groups, hydroxyl groups, methoxy groups, ethoxy groups or benzyloxy groups.

$R_3$ and $R_4$ can be identical or different and are hydrogen, $(C_1-C_6)$-alkyl, $(C_3-C_7)$-cycloalkyl, $(C_1-C_6)$-alkanoyl, $(C_1-C_6)$-alkoxy, halogen and benzyloxy. $R_3$ and $R_4$ can furthermore be the nitro group, the amino group, the $(C_1-C_4)$-mono- or dialkyl-substituted amino group, and the $(C_1-C_6)$-alkoxycarbonylamino function or $(C_1-C_6)$-alkoxycarbonylamino-$(C_1-C_6)$-alkyl function.

Z is O and S.

The designation alkyl, alkanol, alkoxy or alkylamino group for the radicals R, $R_1$, $R_2$, $R_3$, $R_4$, $R_5$, $R_6$, $R_7$ is normally understood as meaning both "straight-chain" and "branched" alkyl groups, where "straight-chain" alkyl groups can be, for example, radicals such as methyl, ethyl, n-propyl, n-butyl, n-pentyl, n-hexyl and "branched alkyl groups" designate, for example, radicals such as isopropyl or tert-butyl. "Cycloalkyl" is understood as meaning radicals such as, for example, cyclopropyl, cyclobutyl, cyclopentyl, cyclohexyl or cycloheptyl.

The designation "halogen" represents fluorine, chlorine, bromine or iodine. The designation "alkoxy group" represents radicals such as, for example, methoxy, ethoxy, propoxy, butoxy, isopropoxy, isobutoxy or pentoxy.

The compounds can also be employed as acid addition salts, for example as salts of mineral acids, such as, for example, hydrochloric acid, sulfuric acid, phosphoric acid, salts of organic acids, such as, for example, acetic acid, lactic acid, malonic acid, maleic acid, fumaric acid, gluconic acid, glucuronic acid, citric acid, embonic acid, methanesulfonic acid, trifluoroacetic acid, succinic acid and 2-hydroxyethanesulfonic acid.

Both the compounds of the formula 1 and their salts are biologically active.

The compounds of the formula 1 can be administered in free form or as salts with physiologically tolerable acids.

Administration can be performed orally, parenterally, intravenously, transdermally or by inhalation.

The invention furthermore relates to pharmaceutical preparations which contain at least one of the compounds of the formula 1 or their salts with physiologically tolerable inorganic or organic acids and, if appropriate, pharmaceutically utilizable excipients and/or diluents or auxiliaries.

Suitable administration forms are, for example, tablets, coated tablets, capsules, solutions for infusion or ampoules, suppositories, patches, powder preparations which can be employed by inhalation, suspensions, creams and ointments.

The preparation processes for the substances can be taken from the examples of German Patent DE 196 36 150 A1. The compounds of general formula I are obtainable according to the following Scheme 1, shown for the synthesis of the compound of Example 1:

Scheme 1

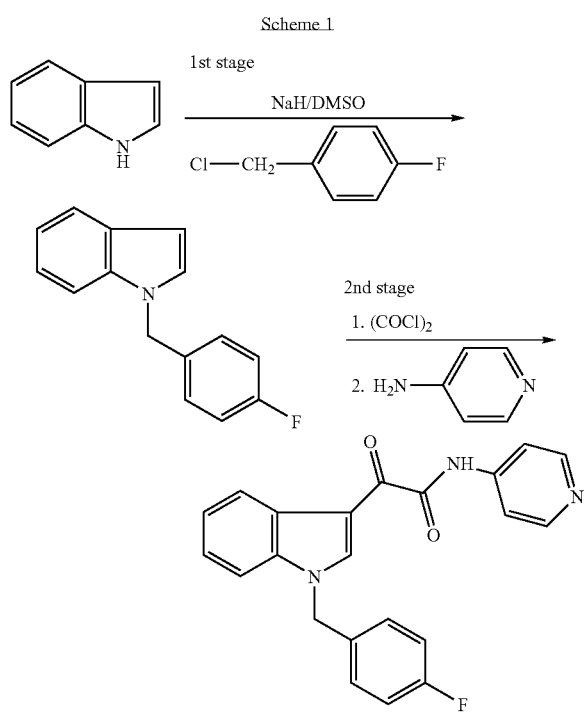

General Procedure for the Preparation of the Compounds of the General Formula I According to Scheme 1

1st Stage

The indole derivative, which can be unsubstituted or mono- or polysubstituted on C-2 or in the phenyl structure, is dissolved in a protic, dipolar aprotic or nonpolar organic solvent, such as, for example, isopropanol, tetrahydrofuran, dimethyl sulfoxide, dimethylformamide, dimethylacetamide, N-methylpyrrolidone, dioxane, toluene or methylene chloride and added dropwise to a suspension of a base in a molar or excess amount prepared in a 3-necked flask under an $N_2$ atmosphere, such as, for example, sodium hydride, powdered potassium hydroxide, potassium tert-butoxide, dimethylaminopyridine, or sodium amide in a suitable solvent. The desired alkyl, aralkyl or heteroalkyl halide, if appropriate with addition of a catalyst, such as, for example, copper, is then added and the mixture is reacted for some time, for example. 30 minutes to 1.2 hours, and the temperature is kept within a range from 0° C. to 120° C., preferably between 30° C. and 80° C., particularly between 50° C. and 65° C. After completion of the reaction, the reaction mixture is added to water, the solution is extracted, for example, with diethyl ether, dichloromethane, chloroform, methyl tert-butyl ether or tetrahydrofuran and the organic phase obtained in each case is dried using anhydrous sodium sulfate. The organic phase is concentrated in vacuo, the residue which remains is crystallized by trituration or the oily residue is purified by recrystallization, distillation or by column or flash chromatography on silica gel or alumina. The eluent used is, for example, a mixture of dichloromethane and diethyl ether in the ration 8:2 (vol/vol) or a mixture of dichloromethane and ethanol in the ration of 9:1 (vol/vol).

2nd Stage

The N-substituted indole obtained by the abovementioned 1st stage procedure is dissolved under a nitrogen atmosphere in an aprotic or nonpolar organic solvent, such as, for example, diethyl ether, methyl tert-butyl ether, tetrahydrofuran, dioxane, toluene, xylene, methylene chloride or chloroform and added to a solution, prepared under a nitrogen atmosphere, of a simply molar up to 60 percent excess amount of oxalyl chloride in an aprotic or nonpolar solvent, such as, for example, in diethyl ether, methyl tert-butyl ether, tetrahydrofuran, dioxane, toluene, xylene, methylene chloride or chloroform, the temperature being kept between –5° C. and 20° C. The reaction solution is then heated at a temperature between 10° C. and 130° C., preferably between 20° C. and 80° C., particularly between 30° C. and 50° C., for a period of 30 minutes up to 5 hours and the solvent is then evaporated. The residue of the indolyl-3-glyoxylic acid chloride formed in this manner which remains dissolved in an aprotic solvent such as, for example, tetrahydrofuran, dioxane, diethyl ether, toluene or alternatively in a dipolar aprotic solvent, such as, for example, dimethylformamide, dimethylacetamide or dimethyl sulfoxide, cooled to a temperature between 10° C. and –15° C., preferably between –5° C. and 0° C., and treated in the presence of an acid scavenger with a solution of the primary or secondary amine in a diluent.

Possible diluents are the solvents used above for the dissolution of the indolyl-3-glyxoylic acid chloride. Acid scavengers used are triethylamine, pyridine, dimethylaminopyridine, basic ion exchanger, sodium carbonate, potassium carbonate, powdered potassium hydroxide and excess primary or secondary amine employed for the reaction. The reaction takes place at a temperature from 0° C. to 120° C., preferably at 20° C. to 80° C., particularly between 40° C. and 60° C. After a reaction time of 1 to 3 hours and standing at room temperature for 24 hours, the hydrochloride of the acid scavenger is filtered, the filtrate is concentrated in vacuo, and the residue is recrystallized from an organic solvent or purified by column chromatography on silica gel or alumina. The eluent used is, for example, a mixture of dichloromethane and ethanol (95:5, vol/vol).

The therapeutically valuable properties found relate specifically to the following advantages:
 no development of resistance was detected
 parameters were detected which are characteristic of the inhibition of metastasis formation (migration)
 parameters were found which confirm the inhibition of neovascularization (angiogenesis)
 in various models, it was not possible to find any neurotoxicity with the N-substituted indole-3-glyoxylamides according to claim 1 in contrast to most antitumor preparations.

The development of resistance which is not present is confirmed in the following pharmacological models and cell cultures:

1. The cytotoxic activity of D-24851 (N-(pyridine-4-yl)-[1-(4-chlorobenzyl)-indole-3-yl]glyoxylamide) on the MDR (multidrug-resistant) leukemia cell line of the mouse L 1210/VCR is not altered in vivo or in vitro. See FIGS. 1, 2 and 3.

D-24851 has an unchanged cytotoxic activity against the multidrug-resistant mouse leukemia cell subline L1210/VCR in contrast to Taxol, doxorubicin, vincristine, or epothilone B.

FIG. 1 shows the cytotoxic action of compound D-24851 against MDR murine leukemic sublime L1210/VCR.

Figure 2:
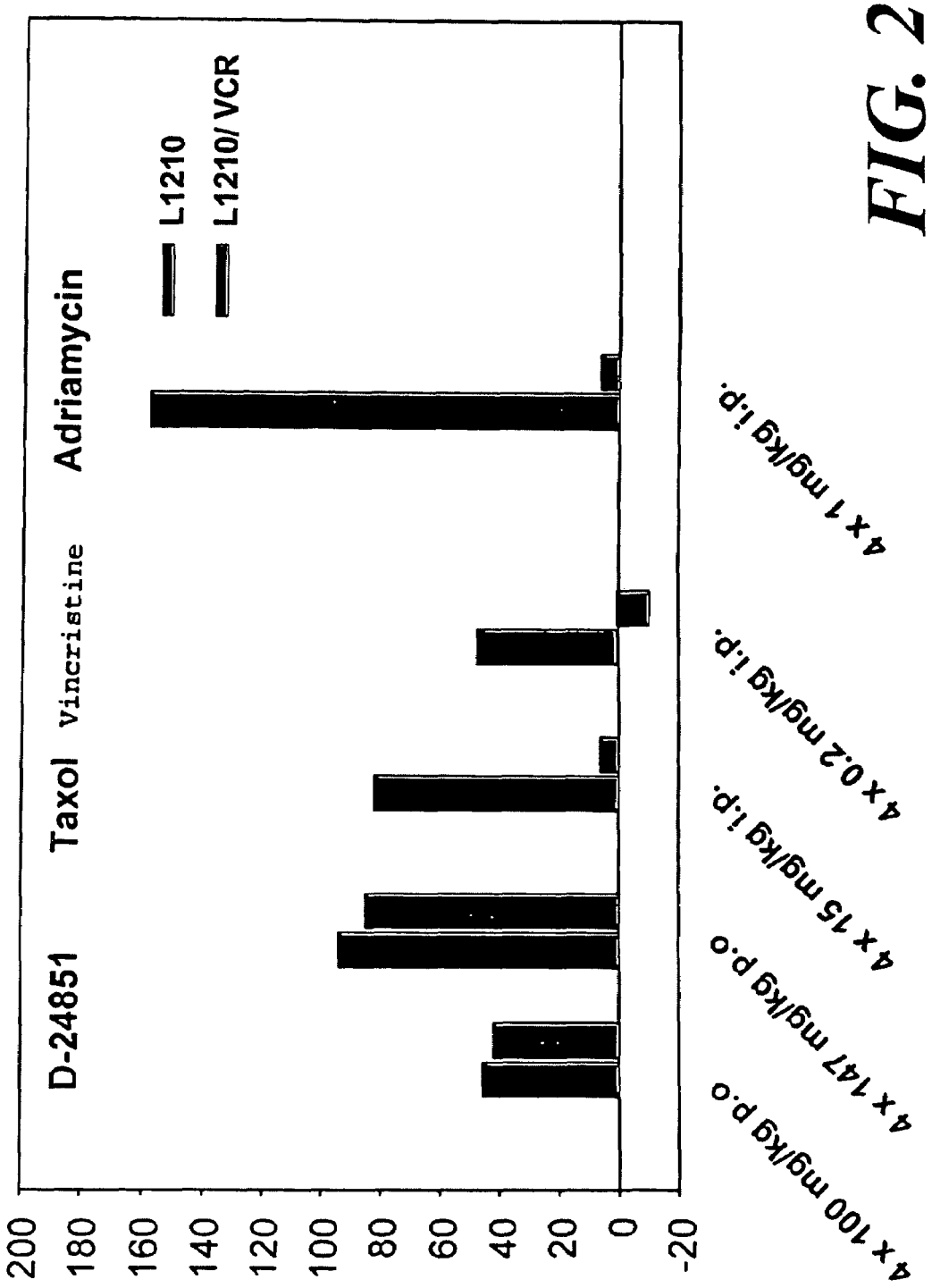

FIG. 2 demonstrates the action of compound D-24851 on a multidrug-resistant tumor.

FIG. 3 shows the influence on the multi-drug-resistant murine leukemia L1210 (dose 10% of the LD. Sub. 50).

Figure 4:
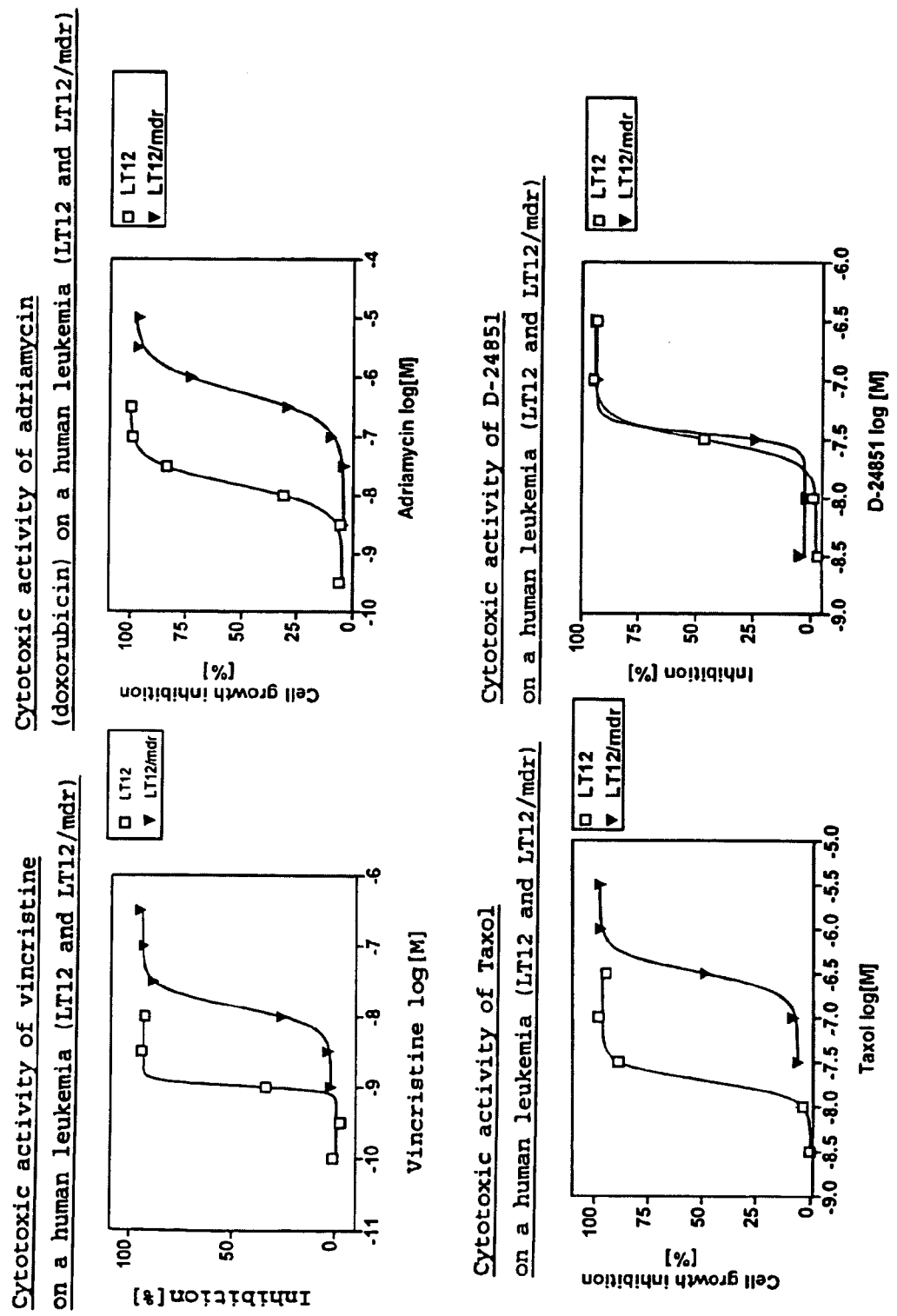

FIG. 4 compares the effect compound D-24851 on human leukemia cells with the effect of other neoplastic agents on the same leukemia cells.

Figure 5:
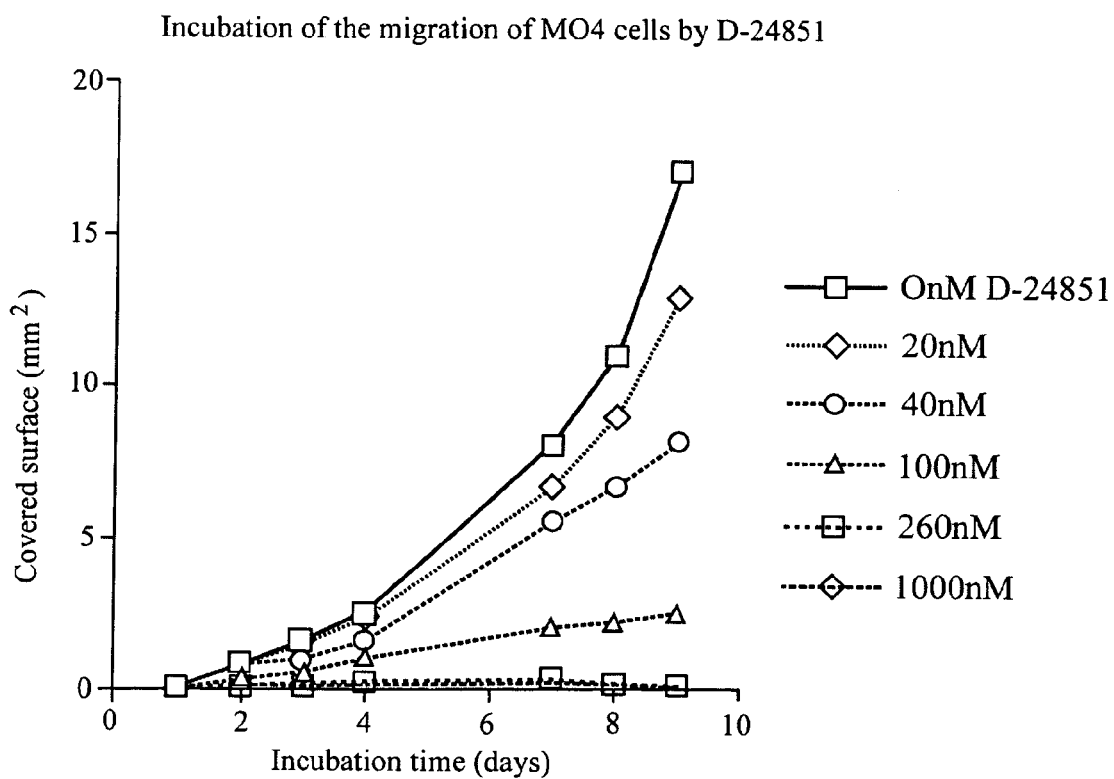

FIG. 5 shows the inhibition of migration of MO4 cells by compound D-24851.

Figure 7:
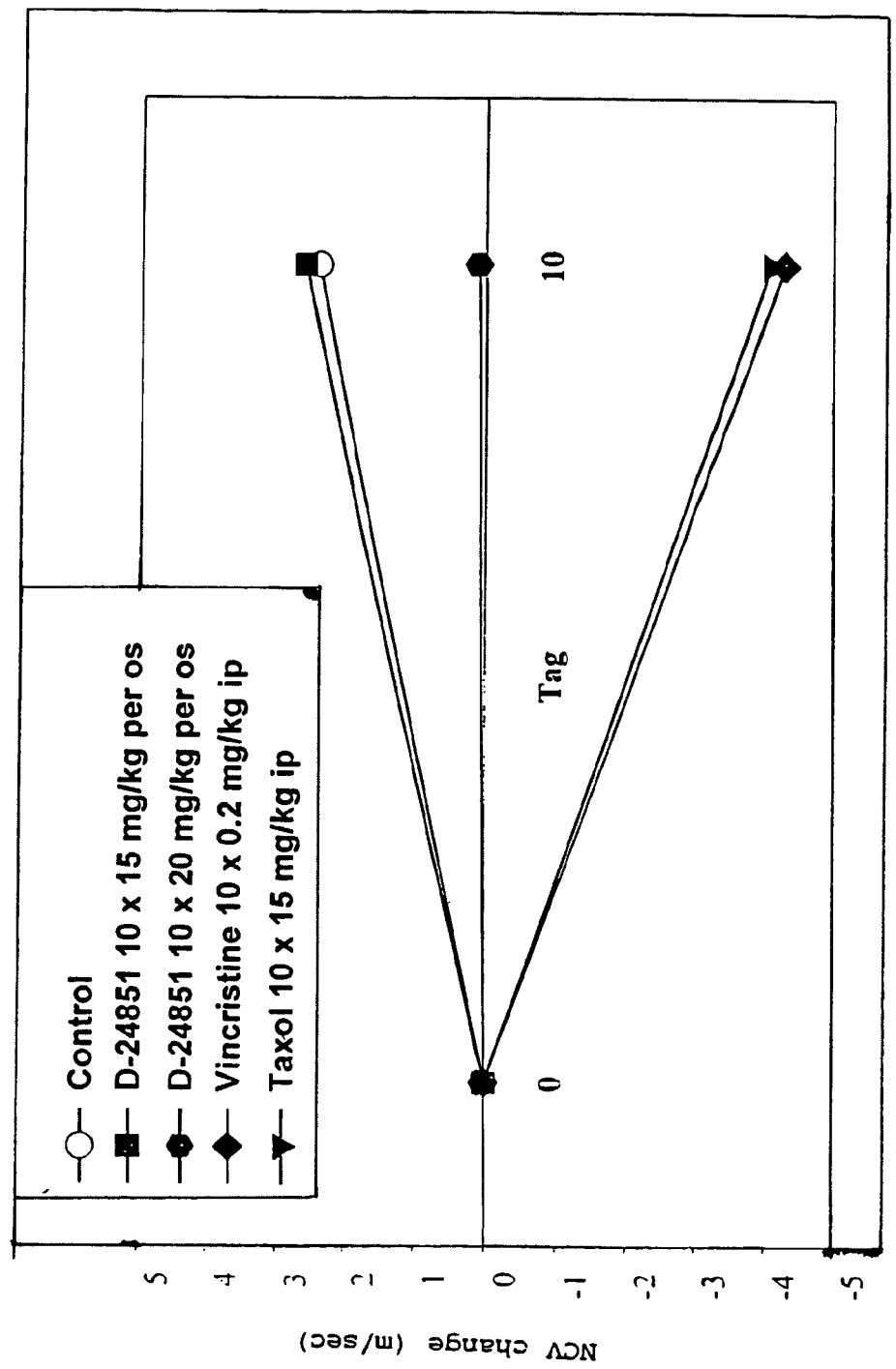

FIG. 6 shows a comparison of neurotoxicity induced by compound D-24851 versus other neoplastic agents, FIG. 7 shows the influence of compound D-24851 on nerve conduction velocity in rat, FIG. 8 compares angiogenesis in human endothelial cells in compound D-24851-treated cells versus DMSO (44 hours after induction of angiogenesis), FIG. 9 compares angiogenesis in human endothelial cells in compound D-24851-treated cells versus DMSO (22 hours after induction of angiogenesis).

Experimental Procedure:

The mouse leukemia cell line L 120 was adapted to vincristine. The unadapted (L 1210) and the adapted (L 1210/VCR) cells were exposed to cytostatic agents and the cell growth, which was determined by the metabolic activity, was determined (XTT test). The curves which connect the XTT datapoints were calculated using a nonlinear regression program. These experimental results were also confirmed in vitro on the human resistant LT 12/MDR cell line (see FIG. 4).

2. The detection of lack of metastasis formation was afforded by means of inhibition of migration of MO4 cells. See FIG. 5. D-24851 inhibits the migration of MO4 cells in a dose-dependent manner. From this, an anti-invasive and an anti-metastatic action can be derived for D-24851.

The migration ability of MO4 cells can be measured in vitro by inoculating cells into the center of a cell culture dish and determining the migration by means of radius or the covered area of the cells after various days with and without D-24851. FIG. 4 shows that the migration of the cells decreases with increasing D-24851 concentration.

In order to test whether D-24851 also acts antiinvasively, the invasion of MO4 fibrosarcoma cells into chickens' hearts was investigated. It is also seen here that at a concentration of 260 and 1000 nM the invasion is completely inhibited, whereas at lower concentrations the invasiveness of the MO4 cells increases. On the basis of these findings, it is seen that D-24851 inhibits both the migration and the invasion of tumor cells and thereby has a strong antimetastatic potential.

3. From comparison experiments of the compound according to the invention D-24851 with vincristine and Taxol on rats, where ataxia, traction and reaction were assessed (see FIG. 6), it is evident that this compound shows no neurotoxic effect, in contrast to Taxol and vincristine. Furthermore, in comparison to Taxol and vincristine, D-24851 has no negative influence on the nerve conduction velocity (see FIG. 7). This confirms that D-24851, on account of the absence of neurotoxicity, has clearly lower side effects than other chemotherapeutics.

4. From further investigations as shown in FIGS. 8 and 9, it is evident that the compound D-25851 (N-(pyridine-4-yl)-[1-(4-chlorobenzyl)-indole-3-yl]glyoxylamide) has a potential as an angiogenesis inhibitor. As a result of the physiological relationship with tumor growth, angiogenesis inhibitors are simultaneously also agents for the inhibition of tumor growth, in that the formation of new blood vessels, which are intended to feed the tumor, is inhibited. In vitro in an antiangiogenesis model on endothelial cells, D-24851 causes a complete inhibition of vascularization, which is not based on a cytotoxic effect. It can be seen in FIG. 8 that D-24851 almost completely breaks up existing cell-cell contacts due to 0.1 μM/L of D-24851 (see vital staining). Normally, the cells maintain at least partial contact. Cell migration is markedly reduced, many cells are rounded. Lethal staining in a monolayer before angiogenesis induction did not show any increased cell mortality with D-24851. Even in the first 22 hours after induction, no increased cell mortality was yet discernible in comparison with the control (see lethal staining in FIG. 9, white points).

It can be seen in FIG. 8 that D-24851 almost completely breaks up existing cell-cell contacts due to 0.1 μMol/l of D 24851 [sic] (see vital staining). Normally, the cells maintain at least partial contact. Cell migration is markedly reduced, many cells are rounded. Lethal staining in a monolayer before angiogenesis induction did not show any increased cell mortality with D-24851. Even in the first 22 hours after induction, no increased cell mortality was yet discernible in comparison with the control. (see lethal staining in FIG. 9, white points)

The cells originated from human umbilical vein (arterial function). They were employed for the investigation in the third and fourth passage. Angiogenesis is triggered by a natural stimulus. The primary trigger of endothelial migration is a protein which is expressed to an increased extent in vascularizing tissue. The substances are added to the culture medium shortly before induction of angiogenesis.

The concentration for the antiangiogenetic action of D-24851 is markedly below the concentration for the cytotoxic activity. As a result, it is possible to separate the two action qualities (cytotoxic activity and antiangiogenetic action) from one another.

Without wanting to restrict the scope of the invention by the following statements, it can be said that doses from about 20 mg up to 500 mg daily are possible orally. On intravenous administration as an injection or as an infusion, up to 250 mg/day or more can be administered depending on the body weight of the patient and individual tolerability. As a result of the lack of development of resistance and suppression of metastasis, a high effectiveness and wide use of the agents even in tumor-refractory patients can be expected. The antiangiogenesis effect is suitable for additionally suppressing the spread of the tumor. However, the invention also comprises the use of the N-substituted indole-3-glyoxylamides according to claim 1 in further disorders in which an angiogenesis inhibitory effect is functionally desired (e.g. wound healing). In addition, the invention also relates to the fixed or free combination of the N-substituted indole-3-glyoxylamides according to claim 1 with antitumor agents known per se, and also the replacement of antitumor agents which have become ineffective as a result of resistance development by N-substituted indole-3-glyoxylamides according to claim 1.

The invention claimed is:

1. A method of inhibiting multidrug-resistant tumor growth or inhibiting metastasis, in a patient comprising administering to said patient an amount of one or more N-substituted indol-3-glyoxylamides of formula I or a physiologically tolerable acid addition salt thereof effective for inhibiting multidrug-resistant tumor growth or inhibiting metastasis

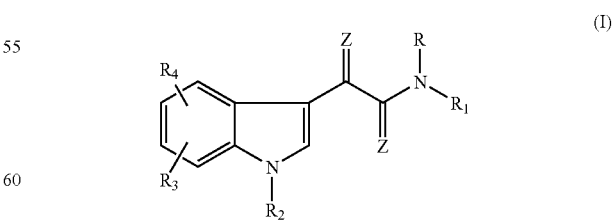

(I)

wherein the radicals $R$, $R_1$, $R_2$, $R_3$, $R_4$, and $Z$ have the following meanings:

$R$ is hydrogen;

$R_1$ is a pyridine structure of formula II

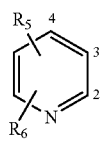

where the pyridine structure is bonded at either the 2, 3, or 4 position of the ring and is optionally substituted by substituents $R_5$ or $R_6$ or both $R_5$ and $R_6$, wherein $R_5$ and $R_6$ can be identical or different and are independently selected from $(C_1$-$C_6)$-alkyl, $(C_3$-$C_7)$-cycloalkyl, $(C_1$-$C_6)$-alkoxy, nitro, amino, hydroxyl, halogen, trifluoromethyl, ethoxycarbonylamino radical and a carboxyalkyloxy group in which the alkyl group has 1-4 C atoms;

$R_2$ is a $(C_1$-$C_6)$-alkyl group, where the alkyl group is monosubstituted by phenyl, which is optionally substituted by one or more substituents selected from halogen, $(C_1$-$C_6)$-alkyl, $(C_3$-$C_7)$-cycloalkyl, a carboxyl group, a carboxyl group esterified with a $C_1$-$C_6$-alkanol, a trifluoromethyl group, a hydroxyl group, a methoxy group, an ethoxy group a benzyloxy group, a 2-quinolyl group or a 2-, 3- or 4-pyridyl group, wherein the 2-quinolyl and 2-, 3-, or 4-pyridyl groups can both in each case be mono- or polysubstituted by halogen, $(C_1$-$C_4)$-alkyl group or $(C_1$-$C_4)$-alkoxy;

$R_3$ and $R_4$ can be identical or different and are independently selected from hydrogen, $(C_1$-$C_6)$-alkyl, $(C_3$-$C_7)$-cycloalkyl, $(C_1$-$C_6)$-alkanoyl, $(C_1$-$C_6)$-alkoxy, halogen, benzyloxy, a nitro group, an amino group, a $(C_1$-$C_4)$-mono or dialkyl-substituted amino group, a $(C_1$-$C_6)$ alkoxycarbonylamino group, and a $(C_1$-$C_6)$-alkoxycarbonylamino-$(C_1$-$C_6)$-alkyl group; and Z is O or S.

2. The method of claim 1, wherein $R_1$ is 4-pyridyl; $R_3$ and $R_4$ are hydrogen; and Z is oxygen.

3. The method of claim 1, wherein one or more of the N-substituted indol-3-glyoxylamides are selected from N-(pyridin-4-yl)-[1-(4-chluorobenzyl)indol-3-yl]glyoxylamide; N-(pyridin-4-yl)-(1-benzylindol-3-yl) glyoxylamide; N-(pyridin-4-yl)-[1-(4-chlorobenzyl)indol-3-yl] glyoxylamide; N-(pyridin-4-yl)-[1-(4-fluorobenzyl)indol-3-yl]glyoxylamide, and their physiologically tolerable acid-addition salts.

4. The method according to claim 1, wherein the acid addition salt is a salt of a mineral acid or a salt of an organic acid.

5. The method according to claim 4, wherein the salt of the mineral acid is selected from hydrochloric acid, sulfuric acid, and phosphoric acid, and the salts or organic acids are selected from acetic acid, lactic acid, malonic acid, maleic acid, fumaric acid, gluconic acid, glucuronic acid, citric acid, embonic acid, methanesulfonic acid, trifluoroacetic acid, succinic acid, and 2-hydroxyethanesulfonic acid.

6. The method according to claim 1, wherein the multidrug-resistant tumor is at least resistant to an antitumor drug selected from taxol, doxorubicin, vincristine, and epothilone B.

7. The method according to claim 1, wherein the one or more N-substituted indol-3-glyoxylamides are used by themselves, in combination with one or more known antitumor agents, or as a replacement therapy for tumors resistant to one or more known antitumor agents.

8. The method of claim 7, wherein the antitumor agent used in combination with the one or more N-substituted indol-3-glyoxylamides is selected from taxol, doxorubicin, vincristine, and epothilone B.

9. The method of claim 7, wherein the antitumor agent for replacement by one or more N-substituted indol-3-glyoxylamides is selected from taxol, doxorubicin, vincristine, and epothilone B.

10. The method according to claim 8, wherein the one or more N-substituted indol-3-glyoxylamides and the one or more antitumor agents are combined together with a pharmaceutically utilizable vehicle, diluent, or excipient.

11. The method according to claim 10, wherein the one or more N-substituted indol-3-glyoxylamides, the one or more antitumor agents, and the pharmaceutically utilizable vehicle, diluent, or excipient are formulated as a tablet, coated tablet, capsule, solution for infusion, ampoule, suppository, patch, powder preparation suitable for inhalation, suspension, cream or ointment.

12. The method of claim 9, wherein the N-substituted indol-3-glyoxylamide is selected from N-(pyridin-4-yl)-[1-(4-fluorobenzyl)indol-3-yl] glyoxylamide; N-(pyridin-4-yl)-(1-benzylindol-3-yl) glyoxylamide; N-(pyridin-4-yl)-[1-(4-chlorobenzyl)indol-3-yl]glyoxylamide; N-(pyridin-4-yl)-[1-(4-fluorobenzyl)indol-3-yl]glyoxylamide, or a physiologically tolerable acid-addition salt thereof.

13. The method of claim 1, wherein the N-substituted indol-3-glyoxylamide is N-(pyridin-4-yl)-[1-(4-chlorobenzyl)indol-3-yl] glyoxylamide or a physiologically tolerable acid-addition salt thereof.

* * * * *

UNITED STATES PATENT AND TRADEMARK OFFICE
CERTIFICATE OF CORRECTION

PATENT NO. : 7,452,910 B2  Page 1 of 1
APPLICATION NO. : 10/686809
DATED : November 18, 2008
INVENTOR(S) : Nickel et al.

It is certified that error appears in the above-identified patent and that said Letters Patent is hereby corrected as shown below:

In claim 3, column 9, line 41, please replace "(4-chluorobenzyl)" with --(4-fluorobenzyl)--.

In claim 12, column 10, line 43, please replace "aphysiologically" with --a physiologically--.

Signed and Sealed this

Twentieth Day of January, 2009

JON W. DUDAS
*Director of the United States Patent and Trademark Office*